(12) United States Patent
Zhang et al.

(10) Patent No.: US 9,110,038 B2
(45) Date of Patent: Aug. 18, 2015

(54) ASYMMETRIC PATTERN PROJECTION APPARATUS

(75) Inventors: Zhuanyun Zhang, Kwai Chung (HK); Ran Shi Wang, Kwai Chung (HK)

(73) Assignee: ASM TECHNOLOGY SINGAPORE PTE LTD, Singapore (SG)

( * ) Notice: Subject to any disclaimer, the term of this patent is extended or adjusted under 35 U.S.C. 154(b) by 1026 days.

(21) Appl. No.: 13/184,698

(22) Filed: Jul. 18, 2011

(65) Prior Publication Data

US 2013/0021464 A1 Jan. 24, 2013

(51) Int. Cl.
*H04N 7/18* (2006.01)
*G01N 21/956* (2006.01)
*G01B 11/25* (2006.01)

(52) U.S. Cl.
CPC .......... *G01N 21/956* (2013.01); *G01B 11/2513* (2013.01)

(58) Field of Classification Search
None
See application file for complete search history.

(56) References Cited

U.S. PATENT DOCUMENTS

| 6,246,067 | B1 * | 6/2001 | Tullis | 250/559.3 |
| 6,509,559 | B1 | 1/2003 | Ulrich et al. | |
| 2001/0033386 | A1 * | 10/2001 | Kranz et al. | 356/601 |
| 2006/0039056 | A1 * | 2/2006 | Lee | 359/212 |
| 2006/0082785 | A1 * | 4/2006 | Janos et al. | 356/503 |

* cited by examiner

*Primary Examiner* — Hung Dang
*Assistant Examiner* — Sunghyoun Park
(74) *Attorney, Agent, or Firm* — Ostrolenk Faber LLP

(57) ABSTRACT

An apparatus for inspection of a surface of a device comprises a projection module operative to project a pattern along a projection axis of the projection module onto the device. An imaging module receives an image of the pattern reflected from the device along an imaging axis of the imaging module onto an image sensor. A lens comprised in the imaging module has a first magnification in a first direction orthogonal to the imaging axis and a second magnification different from the first magnification in a second direction orthogonal to both the first direction and the imaging axis, which produces different fields of view of the image sensor and resolutions of the image in the first and second directions.

10 Claims, 5 Drawing Sheets

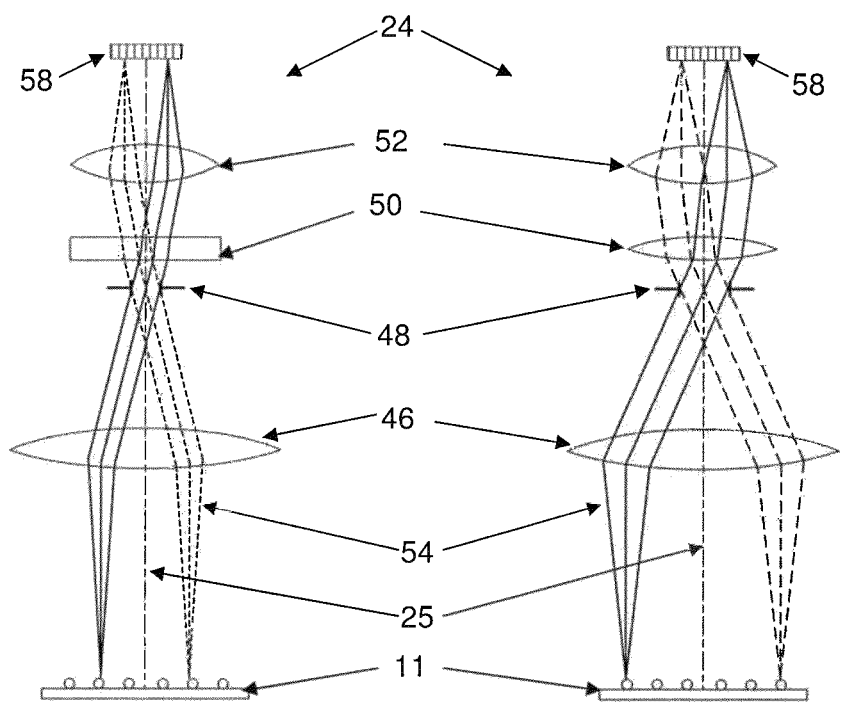
FIG. 9(a)   FIG. 9(b)

ASYMMETRIC PATTERN PROJECTION APPARATUS

FIELD OF THE INVENTION

The invention relates to three-dimensional inspection of semiconductor devices, and in particular to three-dimensional measurement of surface profiles of the same employing high resolution pattern projection and imaging.

BACKGROUND AND PRIOR ART

The need for automated inspection of semiconductor components and manufactured parts has been growing rapidly in recent decades. A typical method uses a charge-coupled device ("CCD") to capture two images of the device that is measured. One image provides planar two-dimensional information of the device, and another image provides height information of the device.

One conventional approach for automated three-dimensional inspection is described in U.S. Pat. No. 6,509,559 entitled, "Binary Optical Grating and Method for Generating a Moiré Pattern for 3D imaging". The invention provides a binary grating in a projection system to generate patterned light, and a three-dimensional imaging system images the patterned light projected onto a surface in order to measure a profile of the surface. The grating includes a binary grating having a cyclical or sine-wave pattern, wherein each cycle includes alternating stripes of varying widths which are substantially clear or substantially opaque.

For such apparatus, the measurement speed depends on the size of a field of view ("FOV") in each image that is captured. A larger FOV can cover a larger area in each captured image and therefore minimizes the number of images that is required to cover the entire semiconductor tray.

However, increasing the inspection speed can be achieved by increasing the size of FOV, but it will be an expensive approach if height measurement accuracy is not to be sacrificed. That is because it requires a larger CCD sensor, optical lenses with larger diameters, larger size of the whole inspection module as well as larger supports for this module in the machine, all of which lead to prohibitive increases in cost.

SUMMARY OF THE INVENTION

It is thus an object of the invention to seek to provide an inspection apparatus which increases the FOV of an inspection device without significantly sacrificing the height measurement accuracy therein in order to improve its inspection speed.

According to a first aspect of the invention, there is provided an apparatus for inspection of a surface of a device, comprising: a projection module operative to project a pattern along a projection axis of the projection module onto the device; an imaging module operative to receive an image of the pattern reflected from the device along an imaging axis of the imaging module onto an image sensor; and a lens comprised in the imaging module having a first magnification in a first direction orthogonal to the imaging axis and a second magnification different from the first magnification in a second direction orthogonal to both the first direction and the imaging axis.

According to a second aspect of the invention, there is provided an apparatus for inspection of a surface of a device, comprising: a projection module operative to project a pattern along a projection axis of the projection module onto the device; an aperture stop comprised in the projection module having a first numerical aperture in a first direction orthogonal to the projection axis and a second numerical aperture different from the first numerical aperture in a second direction orthogonal to both the first direction and the projection axis; and an imaging module operative to receive an image of the pattern reflected from the device along an imaging axis of the imaging module onto an image sensor.

It will be convenient to hereinafter describe the invention in greater detail by reference to the accompanying drawings, which illustrate one embodiment of the invention. The particularity of the drawings and the related description is not to be understood as superseding the generality of the broad identification of the invention as defined by the claims.

BRIEF DESCRIPTION OF THE DRAWINGS

The present invention will be readily appreciated by reference to the detailed description of a preferred embodiment of the invention when considered with the accompanying drawings, in which:

FIGS. 9(*a*) and 9(*b*) illustrate side views of imaging modules with asymmetric magnification in orthogonal directions.

DETAILED DESCRIPTION OF THE PREFERRED EMBODIMENT OF THE INVENTION

Figure 1:
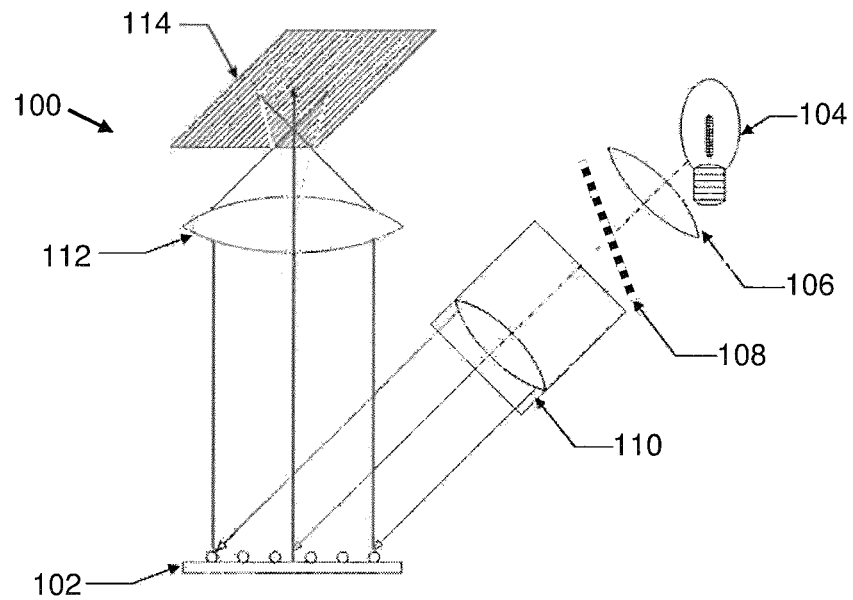
FIG. 1 is a conventional layout of a pattern projection system for three-dimensional measurement.

By way of illustration, FIG. 1 is a conventional layout of a pattern projection system 100 for three-dimensional measurement. The pattern projection system 100 includes a pattern production part which comprises a light source 104, condenser 106, grating 108 and lenses 110 to project a grating image onto a device 102 which is to be measured. The pattern projection system 100 also includes an imaging part which comprises lenses 112 to focus a formed image 114 onto an image plane.

Light that is emitted from the light source 104 passes through the condenser 106 and illuminates the grating 108. A grating glass comprised in the grating 108 has a series of periodic patterns arranged in a conventional cyclical or sinusoidal pattern which is manufactured with high accuracy as regards their line pitch and linearity. A grating image is formed from the grating 108 and is focused by the lenses 110 onto an object plane level. The device 102 is placed onto the object plane level during inspection. If the device 102 to be measured is present, an image of the device 102 with a grating image projected onto it is captured by a sensor of a CCD (not shown) located at the position of the formed image 114 after passing through the lenses 112.

Figure 2:
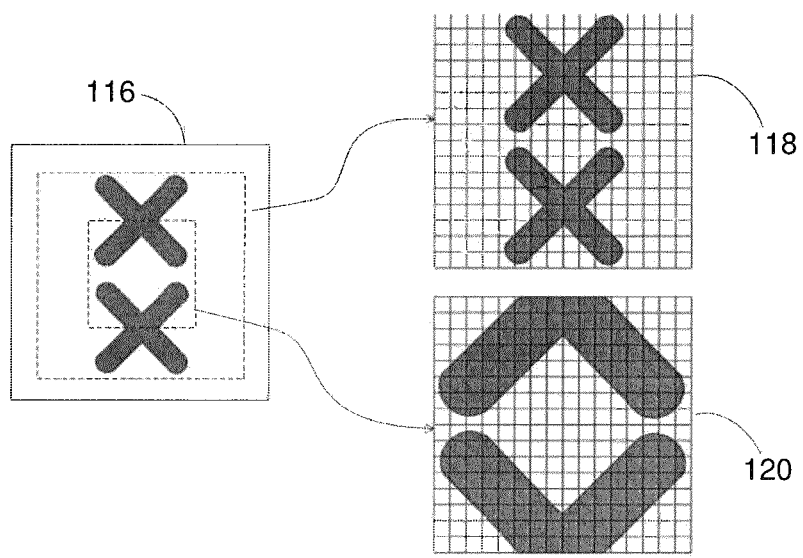
FIG. 2 is an exemplary digital image grabbed by a conventional symmetrical optical system.

FIG. 2 is an exemplary digital image grabbed by a conventional symmetrical optical system. An example of a test pattern 116, together with images 118, 120 of the test pattern 116 obtained by a digital sensor are shown. Illustrated are an image 118 obtained by a digital sensor with a lower magnification factor, as well as another image 120 obtained by a digital sensor with a higher magnification factor. In the conventional pattern projection system 100, due to the higher imaging resolution that is required to obtain detailed information for achieving more accurate height measurement, correspondingly higher optical magnification is needed. Since there is a consistent magnification factor of the lens 112 in both a fringe direction and a pitch direction that is orthogonal to the fringe direction (see FIG. 7), the FOV of the pattern projection system 100 would be inherently limited. There is thus a dilemma between achieving higher height measurement accuracy and a larger inspection area.

Figure 3:
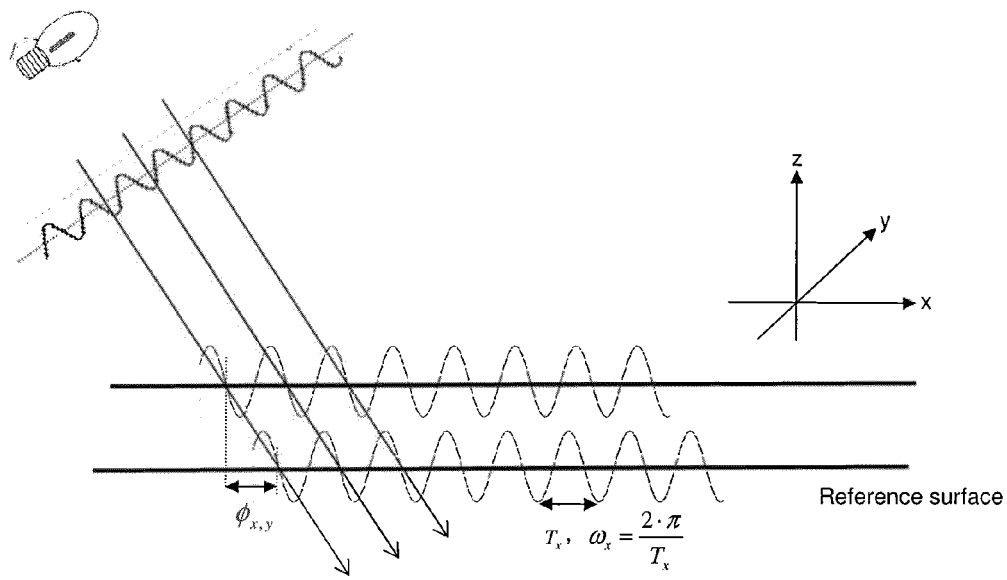
FIG. 3 shows a projected sinusoidal pattern which is periodic both in horizontal and vertical directions.

This dilemma can be solved by the invention of an asymmetric apparatus. Three-dimensional imaging is based on the phase-shifted images as modeled by the following equation, $$I_i(x,y) = R_{x,y} \cdot (1 + M \cos(\theta_i + \omega x \phi_{x,y})) \quad (1)$$

where $I_i(x, y)$ is a target surface intensity at position (x,y) during phase shift $\theta_i$, $R_{x,y}$ is its reflectance and M is the fringe pattern modulation. As shown in FIG. 3, assuming x is along the pitch direction and y is along the fringe direction, $\omega$ is the angular frequency at a reference plane, $\phi_{x,y}$ is phase offset related to the target height at position (x,y). For simplicity of illustration, we assume the lighting intensity is equal to 1 and is uniform over the inspection surface.

By controlling the phase shift of $\theta_i$, for example:

$$\theta_i = 0, \frac{\pi}{2}$$

and $\pi$, for i=0, 1, 2 respectively, we have:

$$\begin{cases} I_0(x, y) = R_{x,y} \cdot (1 + M \cos(\omega x + \phi_{x,y})) \\ I_1(x, y) = R_{x,y} \cdot (1 - M \sin(\omega x + \phi_{x,y})) \\ I_2(x, y) = R_{x,y} \cdot (1 - M \cos(\omega x + \phi_{x,y})) \end{cases} \quad (2)$$

which gives $$\phi_{x,y} = \tan^{-1}\left(\frac{I_0 - 2 \cdot I_1 + I_2}{I_0 - I_2}\right) - \omega x.$$

Figure 4:
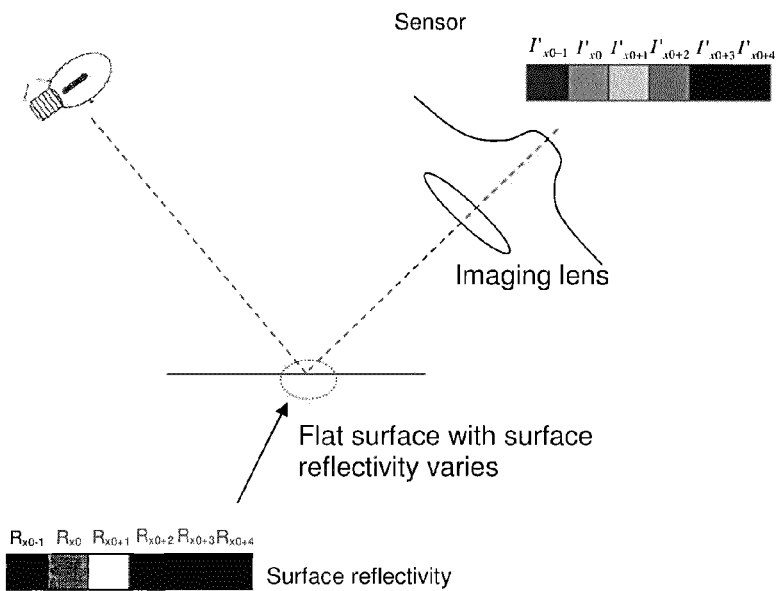
FIG. 4 illustrates a lens blurring effect typically experienced on camera sensors.

FIG. 4 explains how image blur affects the height measurement accuracy and then how the asymmetric apparatus could improve measurement accuracy. As shown in FIG. 4, the image intensity captured on camera sensors is blurred through the imaging lens as expressed as following:

$$I'(x, y) = \sum_{i \in N_x} \sum_{j \in N_y} a_{i,j} \cdot I(x-i, y-j)$$

where I(x,y) is the ideal/high-quality image, I(x,y)' is the real/degraded image captured on the camera sensor after the lens blurring modeled as the convolution with coefficients a(i,j) within a small neighborhood ($N_x$, $N_y$).

Without loss of generality, by assuming the object height, $h_{x,y}$, is constant within a small neighborhood ($N_x$, $N_y$) and then the related phase shift $\phi_{x,y}$ is also constant and denoted as $\phi$, we consider two special cases to elaborate why the optics resolution in the x axis is more important than that in the y axis.

Firstly, by assuming optics blur only in the x direction, we have $$I'(x, y) = \sum_{i \in N_x} a_i \cdot I(x-i, y).$$

According to Equation 2, $$I'_0(x, y) = \sum_{i \in N_x} a_i \cdot R_{x-i,y} + M \cdot \sum_{i \in N_x} a_i \cdot R_{x-i,y} \cdot \cos(\omega(x-i) + \phi)$$

$$I'_1(x, y) = \sum_{i \in N_x} a_i \cdot R_{x-i,y} - M \cdot \sum_{i \in N_x} a_i \cdot R_{x-i,y} \cdot \sin(\omega(x-i) + \phi)$$

$$I'_2(x, y) = \sum_{i \in N_x} a_i \cdot R_{x-i,y} - M \cdot \sum_{i \in N_x} a_i \cdot R_{x-i,y} \cdot \cos(\omega(x-i) + \phi)$$

and $$\phi' + \omega x = \tan^{-1}\left(\frac{I'_0 - 2 \cdot I'_1 + I'_2}{I'_0 - I'_2}\right) = \tan^{-1}\frac{\sum_{i \in N_x} a_i \cdot R_{x-i,y} \cdot \sin(\omega(x-i) + \phi)}{\sum_{i \in N_x} a_i \cdot R_{x-i,y} \cdot \cos(\omega(x-i) + \phi)};$$

Obviously, the estimated $\phi'$ is not equal to the original object height $\phi$ and the error comes from optical blur along the x direction.

On the other hand, for case 2, by assuming optics blur only in the y direction, we have:

$$I'_0(x, y) = \sum_{j \in N_y} a_j \cdot R_{x,y-j} + M \cdot \sum_{j \in N_y} a_j \cdot R_{x,y-j} \cdot \cos(\omega x + \phi)$$

$$I'_1(x, y) = \sum_{j \in N_y} a_j \cdot R_{x,y-j} - M \cdot \sum_{j \in N_y} a_j \cdot R_{x,y-j} \cdot \sin(\omega x + \phi)$$

$$I'_2(x, y) = \sum_{j \in N_y} a_j \cdot R_{x,y-j} - M \cdot \sum_{j \in N_y} a_j \cdot R_{x,y-j} \cdot \cos(\omega x + \phi)$$

Similarly, $$\phi' + \omega x = \tan^{-1}\left(\frac{I'_0 - 2 \cdot I'_1 + I'_2}{I'_0 - I'_2}\right)$$

$$= \tan^{-1}\frac{\sum_{j \in N_y} a_j \cdot R_{x,y-j} \cdot \sin(\omega x + \phi)}{\sum_{j \in N_y} a_j \cdot R_{x,y-j} \cdot \cos(\omega x + \phi)}$$

$$= \tan^{-1}\frac{\sin(\omega x + \phi)}{\cos(\omega x + \phi)}$$

$$= \phi + \omega x;$$

Errors introduced from optical blur along the y direction would be cancelled on height calculation.

Similarly, an electrical output of each cell of the image sensor represents the integration of lighting power falling on the surface area of the cell. Such integration will introduce a low pass filter effect and will produce a blurred digital image. The larger the field of view per cell, the larger will be the blurring effect. Thus, in the asymmetric projection apparatus according to the preferred embodiment of the invention, a high image resolution and therefore a small field of view per cell is designed along the x-direction to produce a lower image blurring effect and higher accuracy of height measurement. Lower resolution is designed along the y-direction to increase the inspection field of view.

Figure 5:
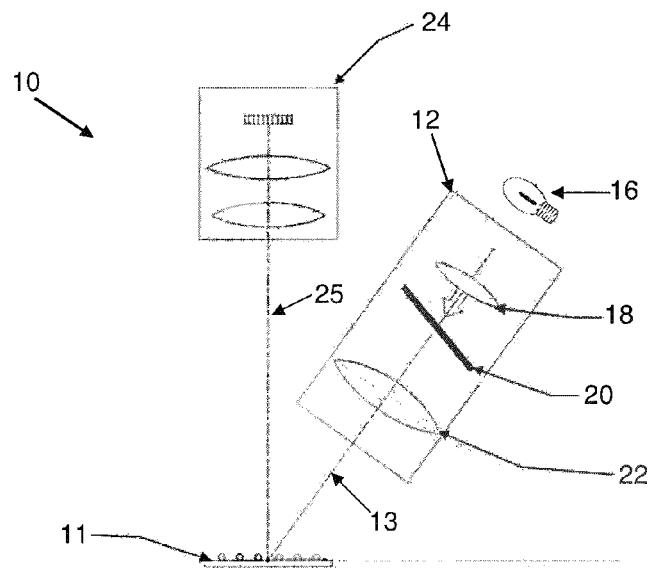
FIG. 5 is a schematic layout of a three-dimensional pattern projection system for three-dimensional measurement according to the preferred embodiment of the invention.

FIG. 5 is a schematic layout of a three-dimensional pattern projection system 10 for three-dimensional measurement according to the preferred embodiment of the invention. The pattern projection system 10 generally comprises a projection module 12 with asymmetric numerical apertures and an imaging module 24 with asymmetric magnification.

The numerical aperture of the lighting projection module 12 is different between two orthogonal axes of the module, that is, along the fringe direction and along the pitch direction respectively. The different numerical apertures can achieve high utilization of lighting energy and maintain a sufficiently sharp pattern to deal with any height variation during measurement, for instance where there is variable device thickness and/or device warpage.

The imaging module 24 is positioned directly above a device 11 to be measured, with an imaging axis 25 of the imaging module 24 being incident on a top surface of the device 11. The imaging module 24 is operative to receive an image of the pattern reflected from the device 11 onto an image sensor comprised in the imaging module 24. The imaging module 24 includes bi-magnification lenses, which provide two different magnifications of an image in two different orthogonal axes.

The lenses comprised in the imaging module 24 has a first magnification in a first direction orthogonal to the imaging axis 25 and a second magnification different from the first magnification in a second direction orthogonal to both the first direction and the imaging axis 25. The different magnifications in the two orthogonal directions result in inconsistent magnifications in the first and second directions in the image received by an image sensor, as well as inconsistency in the image sensor's fields of view in the first and second directions. Therefore, resolutions of an image that are obtained are different in the two orthogonal directions.

The projection module 12 includes a light source 16, condenser 18, grating 20 and lenses 22 to form the grating pattern onto the device 11. The projection module 12 has a projection axis 13 wherein a predetermined pattern comprising periodic patterns spaced from one another is projectable along the projection axis 13 onto the device 11. An asymmetric aperture stop comprised in the projection module 12 has a first numerical aperture in a third direction orthogonal to the projection axis 13 and a second numerical aperture different from the first numerical aperture in a fourth direction orthogonal to both the third direction and the projection axis 13. The projection module 12 may be positioned at various angles relative to the top surface of the device 11.

Figure 6:
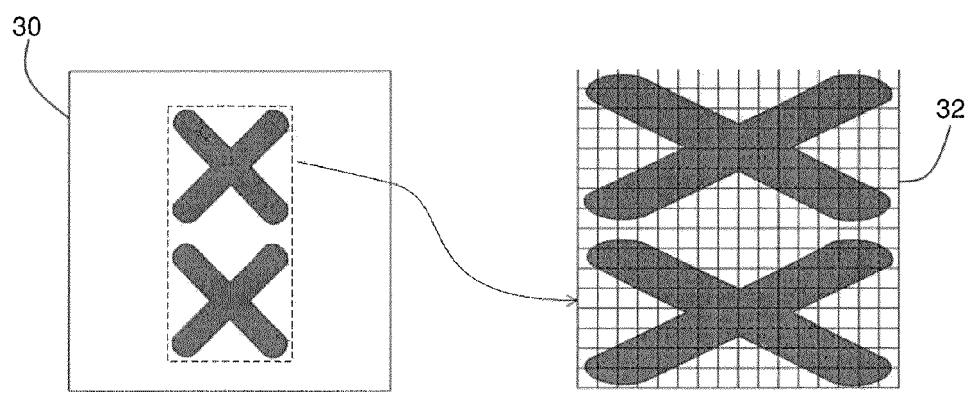
FIG. 6 is an exemplary digital image grabbed by an optical system with asymmetrical magnification according to the preferred embodiment of the invention.

FIG. 6 is an exemplary digital image grabbed by an optical system 24 with asymmetrical magnification according to the preferred embodiment of the invention. It can be seen that a magnification of a test pattern 30 in the captured image 32 is smaller along a first direction (y-axis) as compared to a second direction (x-axis) that is orthogonal to the first direction.

Figure 7:
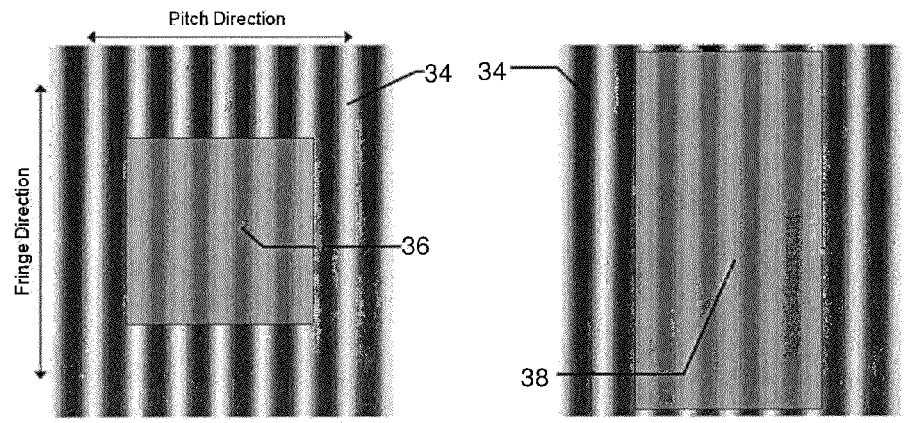
FIG. 7 illustrates a difference in FOV between a conventional pattern projection apparatus and the pattern projection apparatus according to the preferred embodiment of the invention.

Further, FIG. 7 illustrates a difference in FOV 36, 38 between a conventional pattern projection apparatus and the pattern projection apparatus according to the preferred embodiment of the invention. Grating images 34 that are projected are produced from a grating having a pitch direction comprising periodic patterns spaced from one another and a fringe direction which is orthogonal to the pitch direction. In the conventional apparatus, a field of view 36 of a projected grating image 34 is smaller than a comparative field of view 38 of the projected grating image 34 obtained according to the preferred embodiment of the invention when maintaining similar height accuracy.

Figure 8:
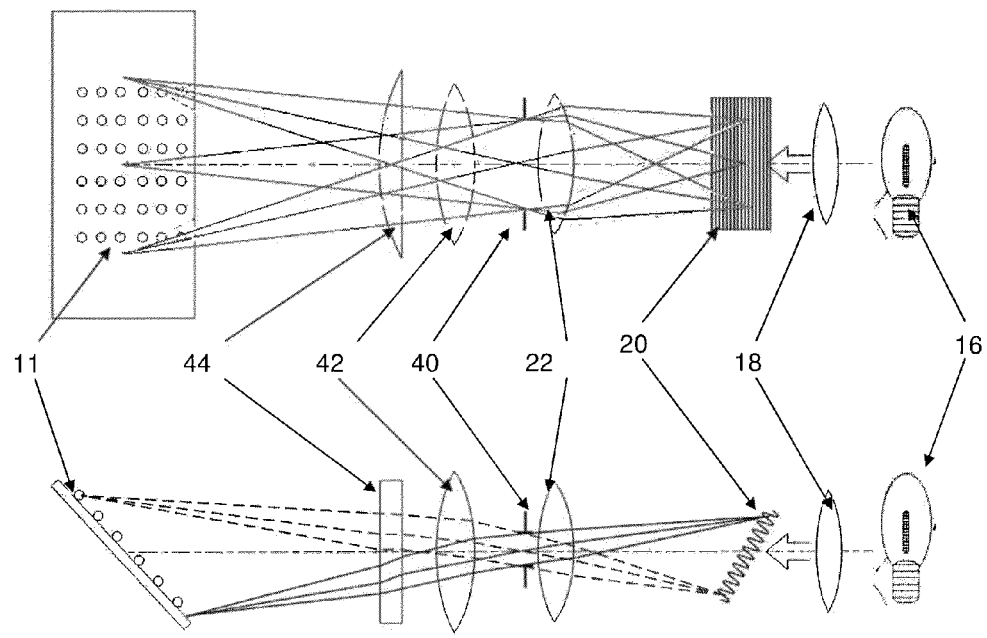
FIG. 8 illustrates a projection system with asymmetric numerical apertures in orthogonal directions.

FIG. 8 illustrates a projection system with asymmetric numerical apertures in orthogonal directions. The projection module which produces grating images 34 from a light source 16 emits lighting through a condenser 18 and grating 20. The grating image 34 passes through the asymmetric aperture stop 40 which has different numerical apertures along first and second orthogonal axes which produces a modified grating image onto the device 11. Preferably, its numerical aperture in a direction parallel to the fringe direction is larger than its numerical aperture in a direction parallel to the pitch direction.

The frequency of the projected grating image 34 in a direction parallel to the pitch direction is high, so that the numerical aperture value of the axis along the pitch direction of the asymmetric aperture stop 40 is smaller. This can maintain an in-focus grating image for height measurement with a large depth of field. On the other hand, the frequency of the projected grating image in a direction parallel to the fringe direction is zero (DC frequency), so the numerical aperture value of the axis along the fringe direction of the asymmetric aperture stop 40 is larger, which provides high lighting energy without any quality loss of the grating image 34. Therefore, the projection module 12 can increase the lighting energy utilization with an asymmetric numerical aperture design and can illuminate with enough lighting energy on the object for highlighting certain desired features for further measurement.

Asymmetric magnification in the imaging module will now be explained. In order to provide higher accuracy on height measurement and to increase the field of view of the pattern projection system 10, the apparatus provides a lens design which has different magnification factors in the pitch and fringe directions. Lenses are configured such that their magnification in a direction parallel to the pitch direction is higher than their magnification in a direction parallel to the fringe direction. As a result, the image that is obtained has a smaller distance per pixel (which leads to higher resolution) in the pitch direction, but has a larger distance per pixel (which leads to lower resolution) along the fringe direction. The resolution along the fringe direction will be reduced to enlarge the accessible field-of-view and the resolution along pitch direction will be kept at high resolution to maintain height measurement accuracy. The field of view can therefore be enlarged and little is sacrificed as regards height measurement accuracy.

FIGS. 9(a) and 9(b) illustrate side views of imaging modules 24 with asymmetric magnification in orthogonal directions. The bi-magnification is achieved by using asymmetric lenses, which may comprise cylindrical lenses 50, in the lens design.

Light rays are reflected from the device 11 along a light path 54 onto focusing lenses 46. The light rays are made to pass through an aperture stop 48 and cylindrical lenses 50. The cylindrical lenses 50 have different magnifications along their two orthogonal directions or axes. The asymmetric image of the reflected light rays that results are focused by focusing lenses 52 onto an image sensor 58 onto which the image of the grating image 34 (see FIG. 7) appearing on the device 11 is received. The FOV 38 of the imaging module 24 is thereby increased.

It should be appreciated that the three-dimensional pattern projection system 10 according to the preferred embodiment of the invention realizes three-dimensional measurement with high accuracy when scanning the device 11 during inspection. The pattern projection system 10 combines a customized projection module 12 which utilizes modified grating image projection optics, and a modified imaging module 24 to capture the grating image 34 reflected from the device 11 to be measured.

In summary, the apparatus provides high accuracy for height measurement of a device 11 that is measured with the advantage of a shorter inspection time due to the larger field of view that is achievable as compared to conventional apparatus. The lighting set-up in the pattern projection system 10 projects a clear grating image 34 for measurement and causes the illuminated region to fully utilize lighting energy on the device 11.

The invention described herein is susceptible to variations, modifications and/or additions other than those specifically described and it is to be understood that the invention includes all such variations, modifications and/or additions which fall within the spirit and scope of the above description.

The invention claimed is:

1. Apparatus for inspection of a surface of a device, comprising:
a projection module operative to project a pattern along a projection axis of the projection module onto the device;
an imaging module operative to receive an image of the pattern reflected from the device along an imaging axis of the imaging module onto an image sensor; and
a lens comprised in the imaging module having a first magnification in a first direction orthogonal to the imaging axis and a second magnification different from the first magnification in a second direction orthogonal to both the first direction and the imaging axis,
wherein the first magnification in the first direction of the lens is larger than the second magnification in the second direction, so as to achieve an asymmetric magnification of the image of the pattern that is reflected from the device, whereby magnification of the image of the pattern is larger in the first direction than in the second direction.

2. Apparatus as claimed in claim 1, wherein the projection module for producing the pattern further comprises a grating having a pitch direction comprising periodic patterns spaced from one another and a fringe direction orthogonal to the pitch direction.

3. Apparatus as claimed in claim 2, wherein the lens comprised in the imaging module is configured such that its magnification in a direction parallel to the pitch direction is higher than its magnification in a direction parallel to the fringe direction.

4. Apparatus as claimed in claim 1, wherein the lens comprised in the imaging module is a bi-magnification lens.

5. Apparatus as claimed in claim 4, wherein the lens is a cylindrical lens.

6. Apparatus as claimed in claim 1, wherein resolutions of the image received on the image sensor are different in the first and second directions.

7. Apparatus as claimed in claim 1, further comprising an asymmetric aperture stop in the projection module having a first numerical aperture in a third direction orthogonal to the projection axis and a second numerical aperture different from the first numerical aperture in a fourth direction orthogonal to both the third direction and the projection axis.

8. Apparatus as claimed in claim 7, wherein the asymmetric aperture stop is incorporated in the projection module.

9. Apparatus as claimed in claim 7, wherein the asymmetric aperture stop comprised in the projection module provides a higher lighting energy utilization in the third direction and a pattern with an image having sufficient sharpness for height measurement in the fourth direction.

10. Apparatus as claimed in claim 7, wherein the projection module for producing the pattern further comprises a grating having a pitch direction comprising periodic patterns spaced from one another and a fringe direction orthogonal to the pitch direction, and an asymmetric aperture stop comprised in the projection module is configured such that its numerical aperture in a direction parallel to the fringe direction is higher than its numerical aperture in a direction parallel to the pitch direction.

* * * * *